United States Patent [19]

Kubodera

[11] Patent Number: 4,851,394
[45] Date of Patent: Jul. 25, 1989

[54] GLUCOMANNAN/POLYHYDRIC ALCOHOL COMPOSITION AND FILM PREPARED THEREFROM

[75] Inventor: Masao Kubodera, Yokohama, Japan

[73] Assignee: Uni Colloid Kabushiki Kaisha, Kanagawa, Japan

[21] Appl. No.: 948,140

[22] Filed: Dec. 29, 1986

[51] Int. Cl.$^4$ .................... A23C 1/29; A23L 1/04; A23L 1/30
[52] U.S. Cl. ...................... 514/54; 106/162; 106/205; 536/1.1; 536/4.1
[58] Field of Search ................. 514/54; 106/162, 205; 536/1.1, 4.1

[56] References Cited

U.S. PATENT DOCUMENTS

| | | |
|---|---|---|
| 3,928,322 | 12/1975 | Sugiyama et al. ............ 536/1.1 |
| 3,973,008 | 8/1976 | Sugiyama et al. ............ 424/195.1 |
| 4,165,392 | 8/1979 | Kawai et al. ............ 426/802 |
| 4,336,145 | 6/1982 | Briscoe ............ 524/45 |
| 4,393,086 | 7/1983 | Masuyama ............ 424/74 |
| 4,427,704 | 1/1984 | Cheney et al. ............ 426/104 |
| 4,466,890 | 8/1984 | Briscoe ............ 252/314 |
| 4,623,394 | 11/1986 | Nakamura et al. ............ 106/205 |
| 4,632,832 | 12/1986 | Okonogi et al. ............ 426/250 |
| 4,676,976 | 6/1987 | Toba et al. ............ 424/485 |
| 4,747,881 | 5/1988 | Shaw et al. ............ 424/498 |

FOREIGN PATENT DOCUMENTS

| | | |
|---|---|---|
| 208313 | 1/1987 | European Pat. Off. . |
| 3335593 | 4/1985 | Fed. Rep. of Germany . |
| 60-55039 | 3/1985 | Japan . |
| 6511675 | 9/1965 | Netherlands . |

*Primary Examiner*—Ronald W. Griffin
*Attorney, Agent, or Firm*—Wenderoth, Lind & Ponack

[57] ABSTRACT

The invention provides a composition having a complex network structure that is formed by mixing glucomannan and optionally another natural polysaccharide with a polyhydric alcohol such as glycerin or a concentrated water solution thereof in the presence or absence of an alkali. When dissolved in water, this composition forms an aqueous solution which can be shape and dried into a film. This film may be eaten directly. Alternatively, it may serve as the shell of a soft capsule or may be used as a food packaging material that is edible together with the food being packaged. The film can also be used as a semipermeable membrane for separating a low-molecular weight substance from a high-molecular weight substance. Other uses of the film include a casing for use in the manufacture of smoked food products and a wound dressing.

26 Claims, No Drawings

4,851,394

GLUCOMANNAN/POLYHYDRIC ALCOHOL COMPOSITION AND FILM PREPARED THEREFROM

BACKGROUND OF THE INVENTION

The present invention relates to a composition having a complex network structure that is formed by mixing glucomannan and optionally another natural polysaccharide with a polyhydric alcohol such as glycerin or a concentrated solution thereof in the presence or absence of an alkali. The present invention also relates to a film prepared from this composition.

The composition of the present invention can be dissolved in water to form a viscous solution. A film formed of this composition is water-resistant and maybe given greater strengthand heat-resisting property. The film finds utility in various applications such as edible films, semipermeable membranes for separating low-molecular weight materials from those having high molecular weights; wound dressings, and the shells of soft capsules.

The principal use of glucomannan has been to produce konjak by reacting it with an alkali in an aqueous solution, then heating the reaction product to form a gel. The gel formed by this method has an inhomogeneous structure and finds no utility other than as konjak. Other natural polysaccharides have been used in an aqueous solution as thickeners, gelling agents, water retainers, stabilizers, dispersants, emulsifiers, binders, etc.

Compounds having multiple hydroxyl groups as exemplified by polyhydric alcohols, sugar alcohols, monosaccharides, dissaccharides and oligosaccharides have been used solely as additives such as sweeteners, humectants, softening agents and plasticizers. Moreover, these compounds have been used singly and no attempt has been made to allow the natural polysaccharides to react directly with polyhydric alcohols in the presence of a small amount of water.

Edible films currently available include starch-based waters, gelatin-based collagen film, and pullulan films. All of these films except those based on gelatin lack resistance to water. Even gelatin films lack high resistance to acid, alkalies and heat. Films formed of cyclodextrins or special proteins obtained by extracting nucleic acids, cell membranes, etc. from yeasts are expensive and their high cost is not justified by corresponding improvements in water resistance, heat resistance and strength.

In the production of smoked meat products such as hams and sausages, semipermeable membranes such as those made of animal guts, regenerated cellulose or cellulose derivatives are used to allow the fragrant and seasoning components in the smoke to penetrate into the meat. However, the supply of animal guts is not abundant and, in addition, they lack strength and are not uniform in size. The supply of regenerated cellulose and cellulose derivatives is also limited because strict regulations against pollution has rendered the construction of new plants practically impossible.

Gelatin has heretofore been used as the shell material of soft capsules for containing drugs, flavors or seasonings but the use of gelatin is limited to applications where oily substances are employed.

Electrolytes or low-molecular weight materials have been separated from high-molecular weight materials by such means as electrodialysis, reverse osmosis, and ionexchange membrane technology. However, these methods use a large number of electrodes or require high pressures so that the equipment for practicing these methods is becoming more and more complex. In order to desalt foods by these methods, large-sized equipment is necessary and it often occurs that other seasoning components eliminated as well as the sodium salt with the result that the taste of the food is impaired.

In the treatment of skin losses due to burns or other external injuries, the affected area is temporarily covered to prevent loss of water or body fluids from the wound, or any exudate from the wound is displaced to prevent bacterial infection so that the formation of granulations and the epidermis is promoted. The films which have been used or attempted to be used for these purposes are formed of such materials as silicone rubber, poly-E-caprolactone, poly (vinyl alcohol), poly-amino acids, fibrin membranes, collagen, polyurethane and pigskin.

However, freeze-dried pigskin and other polyamino acid based wound dressings are all made of polypeptides which are subject to biochemical decomposition. In order to avoid the adverse effects of the degradation products which are liberated, these wound dressings have to be replaced at short intervals, typically every other day. However, replacement of the wound dressing involves much pain for the patient. Furthermore, the film itself has insufficient strength to attain satisfactory coverage. Wound dressings made of synthetic resins such as polyurethane and silicone rubber do not have sufficient affinity for the wound surface to achieve satisfactory permeation to oxygen and water. Normal skin generally allows water to be evaporated in an approximate amount of 350 g/m$^2$ per day, but it has been difficult to prepare synthetic resin films that exhibit this amount of water evaporation and yet have sufficient strength.

It has been proposed to prepare a composite wound dressing by laminating a polyamino acid based film with a synthetic resin film but this composite film still suffers from the defects of the respective film components.

SUMMARY OF THE INVENTION

The present inventors have found that if glucomannan, either independently or in combination with other natural polysaccharides, is mixed with a compound having multiple hydroxyl groups or with a concentrated solution thereof in the presence or absence of an alkali, the respective components react with each other to form a composition having a dense three-dimensional structure. The present inventors have also found that a viscous solution formed by dissolving this composition in water has unique physicochemical properties that have been unattainable by glucomannan, other natural polysaccharides or polyhydric alcohols, and that various products having the characteristics shown below can be prepared from this composition. The present invention has been accomplished on the basis of these findings.

Firstly, edible films having desirable properties such as water resistance, heat resistance and strength can be prepared from the above-described viscous aqueous solution either directly or after being mixed with other foods or food materials. These prepared films may be eaten as such or used as edible food packages.

Secondly, the viscous aqueous solution may be dried into film form and the resulting film may be used in the production of processed meat products (e.g. hams and sausages) as semipermeable membranes having sufficient strength and heat resistance to withstand smoking conditions.

Thirdly, the viscous aqueous solution may be processed to form a film that is suitable for use as the shell of a soft capsule, and using this film, soft capsules capable of confining non-oily drugs, health foods, seasonings or flavors can be prepared.

Fourthly, the film made from the viscous aqueous solution also serves as a high-performance filter medium that is capable of efficient separation of low-molecular weight substances from high-molecular weight substances at reasonably low pressures.

Fifthly, the membrane formed by drying the viscous aqueous solution into film form is a superior wound dressing that achieves close contact with the skin and exhibits superior vapor and oxygen permeation without undergoing any biodegradation during prolonged attachment to the skin.

Sixthly, the viscous aqueous solution cools to provide a gel-like or semifluid foodstuff having unique properties.

DETAILED DESCRIPTION OF THE INVENTION

The glucomannan used in the preparation of the composition of the present invention is the polysaccharide naturally occurring in *Amorphophallus Koniac K. Koch* which is the rhizome of a plant belonging to *Colocasia antiquorum*; it is composed of particles referred to as idioblasts which range from 0.5 to 1.05 mm in length and from 0.37 to 0.5 mm in breadth. The chemical structure of glucomannan is a chain of a 1:2 mixture of glucose and mannose with acetyl and phosphate groups forming pendant ester linkages.

Illustrative polyhydric alcohols that can be used in the present invention are polhydric alcohols in the narrow sense of the term such as propylene glycol and glycerin. These polyhydric alcohols are liquid and may be directly used; however, because of their high hygroscopicity they contain water and are in the form of concentrated aqueous solutions. Moreover they can be used as water solution of concentration in the range of 30 to 90%. Illustrative sugar alcohols include sorbitol, mannitol, maltitol, zylytol and saccharified products of reducing sugar. Illustrative monosaccharides include glucose, fructose, galactose and xylose. Illustrative disaccharides are saccharose, maltose and lactose. Starches such as sweet potato, potato and corn that have been decomposed with enzymes or acids are usable as oligosaccharides, and include di-, tri-, tetra-, penta- and hexasaccharides. The polyhydric alcohols listed above, both in the broad and narrow sense of the term, which are in a powder form at ordinary temperatures, are used as aqueous solutions having concentrations in the range of 30-90 wt%, preferably 50-80 wt%, more preferable 65-75 wt%.

Other natural polysaccharides that may be used in the present invention include the following:

alginic acid which is an intracellular polysaccharides in brown algae, sodium alginate, propylene glycol ester of alginic acid, and agar;

carrageenan which is an intracellular polysaccharide in red algae and is hydrolyzed into D-galactose and D-galactose sulfate ester;

locust bean gum which is a polysaccharide that is present in the seeds of leguminous locust bean and carob and which is chiefly composed of galactomannan;

guar gum that is a polysaccharide present in the seed of leguminous guar and which is hydrolized into galactose and mannose;

tamarind seed polysaccharide which is a polysaccharide present in the seed of leguminous *Tamarindus indica* and which is hydrolized into glucose, zylose and galactose;

pectin which is a generic term for a group of polysaccharides that are the materials of construction of the cell walls of plants such as fruit and vegetables and which are hydrolyzed in to galacturonic acid;

xanthan gum is a polysaccharide produced by the microorganism *Xanthomonas campestris* during fermentation in the presence of glucose and other appropriate essential elements;

chitin which is one kind of mucopolysaccharide;

pullulan which has a repeating unit of $\alpha$-1,6 linkage derived from maltotriose; and cellulose, cyclodextrin and starches.

These natural polysaccharides are optionally used in amounts of 0.05–20 parts by weight, preferably from 0.1 to 10 parts by weight, per part by weight of glucomannan.

In the present invention, the reaction is preferably carried out in the presence of an alkali. Ordinary inorganic or organic alkaline substances may be employed and suitable ones include: sodium hydroxide, potassium hydroxide, calcium hydroxide, magnesium hydroxide, barium hydroxide, sodium carbonate, potassium carbonate, carcium carbonate, ammonium carbonate, magnesium carbonate, sodium bicarbonate, ammonium bicarbonate, basic amino acids and amines. The addition of these alkalies is generally effective in providing films with improved strength and heat resistance.

Part of the glucomannan and optionally used natural polysaccharides may be replaced by proteins to provide compositions which generally have improved heat resistance. Solutions to these compositions in warm water have good mouth feel and can be readily eaten. Illustrative proteins are soybean protein, wheat protein, milk protein, egg white, collagen, decomposed collagen and microbial proteins. Decomposition products of these proteins, such as polypeptides and amino acids, may also be used.

The present invention is characterized by reacting glucomannan directly with at least one compound selected from among the polyhydric alcohols, sugar alcohols, monosaccharides, disaccharides and oligosaccharides. The component made of at least one compound selected from polyhydric alcohols, sugar alcohols, monosaccharides, disaccharides and oligosaccharides is used in an amount which generally ranges from 0.05 to 10 parts by weight, preferably from 0.10 to 5.0 parts by weight, more preferably from 0.15 to 1.0 part by weight, per part by weight of the powder component made of glucomannan and optionally of other natural polysaccharides and proteins. Generally, a higher content of the polyhydric alcohol renders it difficult for a three-dimensional network to develop.

The reactants are mixed at a temperature generally ranging from 5° to 150° C., preferably from 10° to 100° C., more preferably from 20° to 80° C. Mixing at low temperatures will cause no problem because the intended reaction can be allowed to proceed satisfactorily by heating the mixture in a subsequent step such as drying. Generally, mixing at high temperatures provides a composition having a dense structure whereas a brittle composition having a coarse network results if low mixing temperatures are used.

The composition formed by mixing the starting materials described above is a powder that is usually moist to some extent. A solution of this composition in water is viscous and will solidify irreversibly when left to stand at ordinary temperatures, frozen, refrigerated or heated. The properties, in particular the strength, heat resistance and the temperature for dissolution in water, of the solidified product can be altered by proper adjustment of the combination of the starting materials used. Therefore, the solidified product can be used as a base for semifluid or gel-like foods such as jelly and jam. Films may be formed from the viscous solutions by shaping it into a solidified form of a suitable thickness between 1 and 1,000 $\mu$m by any of the known techniques such as wet casting, freeze-drying and extrusion molding. Some of the films formed by these methods are heat-resistant and heat-sealable. If desired, the viscous solution may be coated or sprayed onto a foodstuff and dried to form an edible film on the food.

Films having thicknesses in the range of 1-1,000 $\mu$m, preferably 2-300 $\mu$m, are useful as semipermeable membranes. In a more preferable embodiment, a thin and reinforced semipermeable membrane can be formed by preparing a thin fibrous product from an appropriate material such as paper, nonwoven fabric, woven fabric or net, then filling the voids in the fibrous product with the filter film of the present invention. Filling of the voids in the thin fibrous product may also be achieved by coating the film with the viscous solution or submerging the film in the solution, followed by drying of the film.

Filtration may be achieved by any known technique such as simple filtering under gravity, ultrafiltration or reverse osmosis. The filter medium may be an assembly of hollow fibers or a module of a spirally wound sheet.

In the simplest way, a foodstuff having high sodium chloride concentration is placed on top of the semipermeable membrane of the present invention which is in contact with an underlying water layer; in the absence of any applied pressure, sodium chloride and other low-molecular weight substances in the upper layer will permeate through the membrane to enter the underlying aqueous layer.

Soy sauce, miso and pickled products contain a large amount of sodium chloride in order to ensure that they can be transported long distances or to achieve various purposes such as storage, preservation or good manufacturing practice. The filter film of the present invention is capable of allowing the sodium chloride content of these food products to be lowered without impairing their taste.

In producing processed meat products such as hams and sausages, the meat wrapped in a semipermeable membrane must be smoked. Conventionally, the semipermeable membrane is formed of regenerated cellulose, cellulose derivatives, alginates, collagen, or sheep or bovine gut. However, as already mentioned, these materials have problems in terms of their physical strength and heat resistance, and in particular, sheep and bovine guts are not uniform in size and shape and suffer from instability in supply.

Fibrous products are usually porous and the films prepared by impregnating or coating them with the edible composition of the present invention serve as ideal casing materials wherein the semipermeable membrane formed of the edible material is reinforced with the fibrous product. Such casing materials may be prepared as follows: a fibrous product of a given width is shaped into a tubular base, which is continuously impregnated with an aqueous solution of the composition of the present invention and dried to form a strong fibrous casing.

The shell of conventional soft capsules is formed from an aqueous solution of gelatin and glycerin and is only capable of confining oily products. The soft capsules formed from an aqueous solution of the composition of the present invention are capable of confining not only oily products but also water-soluble substances and, hence, are applicable to enlarged areas of use, for instance: (1) water-soluble vitamins such as vitamins $B_1$, $B_2$, $B_5$, $B_6$, $B_{12}$, niacin folic acid and vitamin C; (2) nutrients such as liquid glycides, proteins and minerals; (3) diets formed of soft capsules that incorporate liquid seasonings or flavors and which are readily edible after cooking; and (4) cosmetics in soft capsules that are to be punctured with a needle to allow the contents to be used.

Soft capsules may be prepared from the composition of the present invention as follows: the composition is dissolved in water and the solution is allowed to flow out of a spreader box to form a gel which is subsequently shaped into a film form, two sheets of the film thus obtained are passed through a pair of die rolls to adhere to each other; a predetermined amount of the content (ie, fill) is forced with a pump to obtain a capsule form, which is subsequently dried to form a soft capsule.

The film prepared in accordance with the present invention is also useful as an ideal wound dressing. It swells readily upon absorbing body fluids from a wounded site of the human body but its three-dimensional network will remain intact. The film increases in thickness but its area remains the same so as to allow the absorbed moisture to be evaporated from its surface. The film supplies the wound surface not only with moisture but also with the drug applied onto the outer surface of the film; at the same time, the film allows the unwanted exudate to be liberated on its surface. Therefore, the film does not have to be peeled off until after the wound has healed. The thickness of the film used as a wound dressing generally ranges from 1 to 1,000 $\mu$m, preferably form 5 to 200 $\mu$m, more preferably from 7 to 50 $\mu$m.

When the composition of the present invention is dissolved in water, a vicous solution or slurry with a solids content of 2-10% will form and this can be incorporated in a large amount in suitable food materials. The incorporated composition will solidify irreversibly by being left to stand at ordinary temperatures, or when frozen, refrigerated or heated. The properties, in particular the strength, heat resistance and the temperature for dissolution in water of the solidified product can be altered by properly adjusting the combination of starting materials used. Furthermore, the solidifed product retains the flavor of the food material present.

The food materials that can be mixed with the viscous solution or paste of the composition of the present invention are diverse and include: seaweeds; marine products such as shrimp, cuttlefish, fish (e.g. bonito, tuna and salmon), and fish roe; vegetables such as spinach, cabbage, carrot and pumpkin; fruits such as orange, grape, apple and pineapple; meats such as beef, pork, chicken, and corned beef; processed foods such as cheese, jam, mayonnaise and miso; seasonings such as soy sauce and sodium glutamate; as well as spices and flavors such as peanut, almond, mustard, pepper, curry, cocoa, coffee and chocolate.

These food materials may be mixed with the viscous solution or slurry of the composition of the present invention either directly, or after being conditioned for a given particle size or shape, or after being formed into a paste. The mixing ratio of these food materials to the glucomannan/polyhydric alcohol composition of the present invention is not limited to any particular value because it largely depends on the type of food material used or the specific formulation of the composition. It should however be noted that a preferable mixing ratio is such that the mixture can be readily formed into a film, and that the shaped food is easy to handle and does not reveal the mouth feel of the composition.

The aqueous solution of the composition of the present invention is viscous and its properties, in particular its strength, heat resistance and temperature for dissolution in water, can be altered by allowing it to stand at ordinary temperatures, or by freezing, refrigerating or heating the same. Therefore, the aqueous solution, after being shaped into a gelled block of an appropriate hardness, may be mixed with a non-alcoholic beverage such as juice or yogurt or foods, and the resulting mixture can be safely heated without melting to thereby provide a composite dietary product that shows a desirable combination having the sort of mouth feel that is possessed by dissimilar components. There is no particular limitation on the size of the gel block and its hardness varies with the type of base used: if the base is a liquid material such as juice, the moisture content of the block is preferably increased to provide a soft texture, whereas if the base is jelly or any other material that has a certain amount of self-retaining property, its moisture content is decreased to provide a hardness slightly lower than that of the jelly. In either case, the resulting product is composed of two dissimilar materials and yet displays good palatability.

Glucomannan has a complex structure containing various side chains and reactive groups and, because of the presence of many hydroxyl groups at high concentrations, glucomannnan and other natural polysaccharide enter into a reaction to form a complex matrix even under a substantially water-free condition. The matrix forming reaction will be enhanced by the presence of an alkali and an even more complex compound will form. In the presence of both an alkali and water, the development of a threedimensional network is further promoted to form an irreversibly solidified product, which can be processed to provide a characteristic gel-like base or a coating.

The present invention is hereinafter described in greater detail with reference to the following examples to which the scope of the invention is by no means limited and wherein all parts are on a weight basis.

EXAMPLE 1

Eight parts of glucomannan was mixed with 2 parts of glycerin for 15 minuites an 70° C. to form a sample of the composition of the present invention which was a somewhat moist powder. Two parts and a half of this composition were mixed with 97.5 parts of water to form a viscous aqueous solution. This solution was coated onto the peel of orange and dried at 50° C. for 1 hour to provide orange having an edible film coating on its peel. This orange and uncoated orange were stored at 25° C. for 10 days. Thereafter, the appearance of the two oranges and the mouth feel of their pulp were compared. Compared with the uncoated orange, the one having an edible film coat had undergone a smaller degree of water evaporation and oxidation, retained more luster and experienced less surface discoloration. The pulp of the coated orange was fresher and more palatable.

EXAMPLE 2

Three parts of the composition prepared in Example 1 was mixed with 0.04 parts of a vitamin E powder (70% natural vitamin E and 30% emulsifier) and 97 parts of water to form an aqueous solution. An orange whose peel was coated with the resulting aqueous solution as in Example 1 was stored at 25° C. for 15 days together with an uncoated orange. The results of comparison of the two oranges were the same as in Example 1.

EXAMPLES 3–10

The components listed in Table 1 were mixed for 10 minutes at 80° C. in the amounts also shown in Table 1, so as to prepare eight additional samples of the composition of the present invention. Three parts of each of the samples was mixed with 97 parts of water and the resulting aqueous solutions were cast by the wet process to form translucent edible films having thicknesses ranging from 10 to 20 μm. The films prepared in Examples 3 to 6 were water-resistant and stable in the following solutions: aqueous solutions with NaCl concentrations of 5% or more; acidic aqueous solutions with pH of 2.5–4.5; alkaline aqueous solutions with pH of 9.0–12.0; aqueous solutions with ethanol concentrations of 10% or more. The films prepared in Examples 7–10 were not only water-resistant; they were resistant to hot water and stable in aqueous solutions heated to 80–100° C.

TABLE 1

| Example No. | (unit in parts by weight) | | | | | | | |
|---|---|---|---|---|---|---|---|---|
|  | 3 | 4 | 5 | 6 | 7 | 8 | 9 | 10 |
| natural polysaccharide | | | | | | | | |
| glucomannan | 5 | 5 | 5 | 5 | 5 | 5 | 5 | 5 |
| carrageenan | 3 |   |   | 2 |   | 4 |   | 3 |
| agar |   | 2 |   |   |   |   | 1 |   |
| locust bean gum |   |   | 2 |   |   |   |   | 1 |
| xanthan gum |   |   |   | 1 |   | 0.5 |   |   |
| alkali | | | | | | | | |
| calcium carbonate |   |   |   |   |   |   | 0.3 | 0.1 |
| calcium hydroxide |   |   |   |   | 0.05 |   |   |   |
| sodium bicarbonate |   |   |   |   |   |   | 0.5 | 0.3 |
| glycerin |   | 1.5 |   | 1.5 | 1 |   | 1 |   |
| sorbitol (70% aq. sol.) | 1.5 |   |   |   |   | 1 |   |   |
| saccharose (80% aq. sol.) |   |   | 1.5 |   |   |   |   | 1 |

EXAMPLE 11

An edible package film 15 μm thick was formed from a composition having the same formulation as used in Example 3. Stripped lobster (150 g) was wrapped with this film and stored at −25° C. for 3 months. The frozen lobster as wrapped in the film was thawed in a microwave oven and cooked. The cooked lobster had the edible film on it but one did not sense any peculiar feel as a result of the presence of the film.

EXAMPLE 12

An edible film 15 μm thick was formed from a composition having the same formulation as used in Example 8. Vegetable salad with a dressing was sandwiched between two slices of bread. During subsequent storage, the dressing did not permeate into the bread at all. After the storage the bread was eaten; it tasted good and the taste of the edible film was not sensed.

EXAMPLE 13

| Components | Amount (in parts) |
| --- | --- |
| Glucomannan | 5 |
| Sodium bicarbonate | 0.1 |
| Calcium Carbonate | 0.02 |
| Glycerin | 1 |

These components were mixed at 75° C. for 20 minutes. Three parts of the resulting composition were dissolved in 97 parts of water. The aqueous solution was applied continuously to form a uniform coating on the inner surface of a fluoroethylene resin-coated cylindrical pipe having a diameter of 120 mm. The applied coat was dried to form a tubular casing.

Processed meat was packed into the casing at a pressure of up to 2 kg/cm$^2$ without causing its disruption. The packed meat was smoked and sterilized by heating in hot water (80° C.) for 2 hours to produce a satisfactory ham.

EXAMPLE 14

| Components | Amount (in parts) |
| --- | --- |
| Glucomannan | 5 |
| Agar | 0.5 |
| Calcium carbonate | 0.5 |
| Sodium citrate | 0.3 |
| Sorbitol (70% aq. sol.) | 1 |

These components were mixed at 80° C. for 10 minuites. Three parts and a half of the resulting composition were dissolved in 96.5 parts of water to form a viscous aqueous solution. A sheet of porous paper having a thickness of 100 μm was prepared, with wood pulp and cotton linter being used as chief components. The two side edges of the sheet were adhered together to form a tubular base. The wall of this base was impregnated with the previously prepared viscous aqueous solution and dried to form a casing that was formed of a sample of the film of the present invention that had a thickness of 120-130 μm and which was reinforced with a fibrous product.

Processed meat was packed into the casing at a pressure of up to 6 kg/cm$^2$ without causing its disruption. The packed meat was smoked and sterilized by heating in hot water (80° C.) for 2 hours to produce a satisfactory sausage.

EXAMPLE 16

A mixture of gelatin (100 parts) and glycerin (30 parts) was dissolved in 60 parts of water at 75° C. with stirring and defoamed with a vacuum pump. The solution was shaped into a 450 μm thick film on an automatic rotary continuous soft capsule filling machine. A film 25 μm thick that was prepared as in Example 6 was stacked on the inside surface of the 450 μm thick film to form a double-layered film. Two units of this double-layered film were passed between a pair of die rolls to be adhered to each other and an aqueous solution of 30% L-ascorbic acid was forced in with a filling pump to form capsules each containing 500 mg of the fill. The capsules were dried to produce soft capsules.

EXAMPLE 16

| Components | Amount (in parts) |
| --- | --- |
| Glucomannan | 5 |
| Carrageenan | 0.5 |
| Calcium carbonate | 0.12 |
| Glycerin | 1 |

These components were mixed at 70° C. for 30 minutes. Three parts of the resulting composition was dissolved in 97 parts of water to form a viscous aqueous solution. The solution was formed into an edible film 15 μm thick by the wet casting method. As in Example 15, a dual-layered capsule shell was formed by staking this film over a gelatin film. Using this shell, soft capsules each containing 5 g of seasonings for instant chicken soup were produced. On of these soft capsules was mixed well with 150 ml of hot water (90° C.) under agitation; the capsule was disintegrated in the water to provide chicken soup.

EXAMPLE 17

A mixture of gelatin (100 parts) and glycerin (30 parts) was dissolved in 10 parts of water at 75° C. with stirring. The solution was defoamed with a vacuum pump and designated A. In a separate step, 5 parts of glucomannan, 3.5 parts of carrageenan and 1.5 parts of glycerin were mixed at 70° C. to form a sample of the composition of the presnet invention; 3 parts of the composition was dissolved in 97 parts of water to form an aqueous solution which was designated B. An intimate blend of solution A (60 parts) and solution B (40 parts) was fed into an automatic rotary continuous soft capsule filling machine to form soft No. 5 oval capsules by the known rotary die method, with each capsule having confined therein 290 mg of an astringent lotion. Just prior to use, each soft capsule was punctured with a needle to recover to lotion in an amount sufficient for single use.

EXAMPLE 18

| Components | Amount (in parts) |
| --- | --- |
| Glucomannan | 5 |
| Carrageenan | 3 |
| Cellulose | 1 |
| Glycerin | 2 |

These components were mixed at 80° C. for 10 minutes and 2.5 parts of the resulting composition was dissolved in 97 parts of water. The solution was formed into a circular film (thickness, 15 μm; diameter, 29 mm) by the wet casting method. The film was set in a filtration vessel which was filled with 450 ml of tap water in its lower compartment and with 150 ml of soy sauce (18% NaCl) in its upper compartment. The vessel was left to stand at 20° C. for a given period and the contents of NaCl and amino acid nitrogen in the soy sauce were measured at predetermined intervals. The results are shown in Table 2.

TABLE 2

(effective surface area of film: 960.6 mm)

| Time (min) | NaCl (%) | Amino acid $N_2$ | Increase in water content (%) |
|---|---|---|---|
| 0 | 16.4 | 0.91 | 0 |
| 30 | 15.7 | 0.86 | 0.7 |
| 60 | 16.5 | 0.82 | 1.6 |
| 90 | 15.0 | 0.86 | 2.7 |
| 120 | 14.1 | 0.79 | 4.1 |
| 150 | 13.3 | 0.78 | 5.7 |

As Table 2 shows, the NaCl content of the soy sauce decreased with time and this was accompanied by gradual depletion of amino acids and increase in the moisture content. However, most of the amino acids that flowed out were those having low molecular weights such as glycine and alanine and their depletion did not cause any substantial deterioration of the taste of the soy sauce. The soy sauce prepared in accordance with the present invention had a generally mellow taste and its sodium chloride content was low.

EXAMPLE 19

An aqueous solution of the composition used in Example 18 was heated to 70° C. with stirring and applied to a thin sheet of paper (basis weight: 16 g/m²) to form a film having a thickness of 35 μm. This fiber-reinforced film was tested as in Example 18. The results were substantially the same as those obtained in Example 18. The film prepared in this example was superior to that prepared in Example 18 in terms of self-retaining property and tensile strength.

EXAMPLE 20

| Components | Amount (in parts) |
|---|---|
| Glucomannan | 5 |
| Xanthan gum | 0.5 |
| Calcium hydroxide | 0.06 |
| Glycerin | 1 |

These components were mixed at 60° C. for 20 minutes to obtain a sample of the composition of the present invention. Three parts of this composition were dissolved in 97 parts of water and a thin layer of the solution was spread onto a fluoroethylene resin-coated sheet. The coating was freeze-dried by a conventional method to prepare a wound dressing in a film form having a thickness of 12 μm. The film was sterilized, coated with a drug layer and attached to the surface of a wound produced by a third-degree burn. The treatment that ensued consisted of delivering the drug daily onto the surface of the film. Formation of granulations continued steadily without suppuration and in 10 days normal skin tissue was restored, whereupon the film separated from the skin spontaneously.

EXAMPLE 21

An aqueous solution of the composition used in Example 20 was coated onto a nonwoven polyester fabric (basis weight:10 g/m²) and freeze-dried by a known method so as to make a film having a thickness of 30 82 m. This film was used as a wound dressing to cure a burn in accordance with the same regimen as employed Example 20. The results were substantially the same as those obtained in Example 20.

EXAMPLE 22

| Components | Amount (in parts) |
|---|---|
| Glucomannan | 5 |
| Alginic acid | 1 |
| Guar gum | 0.5 |
| Glycerin | 1 |

These components were mixed at 65° C. for 20 minutes to form a sample of the composition of the present invention. Three parts of this composition were dissolved in 97 parts of water. Seventy-five parts of the solution were mixed with 25 parts of a beef fillet and the blend was shaped into an edible film (thickness:25 μm) by the wet casting method. The film was laid down on a slice of bread; the product had a characteristic flavor originating from the blending of the taste of beef with the bread.

EXAMPLE 23

| Components | Amount (in parts) |
|---|---|
| Glucomannan | 5 |
| Tamarind seed polysaccharide | 1 |
| Gelatin | 1 |
| Glucose (80% aq. sol.) | 1 |

These components were mixed at 60° C. for 40 minuites to form a sample of the composition of the present invention. Three parts of this composition were dissolved in 97 parts of water to form a viscous aqueous solution. Eighty parts of this solution were blended with 20 parts of a dried spinach powder (particle size:100-Tylermesh pass) and the blend was shaped into an edible film (15 μm thick) by a known freeze-drying technque. This film was rolled around a bar of cooked rice so as to provide a low-calorie dietary product.

EXAMPLE 24

| Components | Amount (in parts) |
|---|---|
| Glucomannan | 5 |
| Carrageenan | 5 |
| Calcium carbonate | 0.2 |
| Glycerin | 1.5 |

These components were mixed at 70° C. for 30 minutes to form a sample of the composition of the present invention. Five parts of this composition were mixed and kneaded with 95 parts of cocoa paste and the necessary seasonings to make a chocolate mass, which was refined and molded into a sheet. Although conventional chocolate products are soften at 35° C. or higher, the chocolate sheet of the Example 24 did not soften until it was heated to 50° C.

What is claimed is:

1. A glucomannan/polyhydric alcohol composition prepared by uniformly mixing glucomannan and other natural polysaccharides with a concentrated solution of at least one polyhydric alcohol.

2. A composition according to claim 1 wherein said solution of at least one polyhydric alcohol has a concentration of 30–100 wt%.

3. A glucomannan/polyhydric alcohol composition prepared by uniformly mixing glucomannan and other natural polysaccharides with a concentrated solution of a least one polyhydric alcohol in the presence of an alkali.

4. A composition according to claim 3 wherein said solution of at least one polyhydric alcohol has a concentration of 3-100 wt%.

5. A film prepared by a process comprising the steps of:
uniformly mixing glucomannan and other natural polysaccharides with a concentrated solution of at least one polyhydric alcohol;
dissolving the resulting glucomannan/polyhydric alcohol composition in water to obtain a solution;
forming the solution into a film; and
drying the film.

6. A film according to claim 5 which is an edible food packaging material.

7. A film according to claim 5 which is a casing for smoked food products.

8. A film according to claim 7 which is a casing film reinforced with a thin fibrous product.

9. A film according to claim 5 which is a shell for a soft capsule.

10. A film according to claim 5 which is a semipermeable membrane for separating a high-molecular weight substance from a low-molecular weight substance.

11. A film according to claim 10 which is reinforced with a thin fibrous product.

12. A film according to claim 5 which is a wound dressing.

13. A film according to claim 12 which is reinforced with a thin fibrous product.

14. A film prepared by a process comprising the steps of:
uniformly mixing glucomannan and other natural polysaccharides with a concentrated solution of at least one polyhydric alcohol in the presence of an alkali;
dissolving the resulting glucomannan/polyhydric alcohol composition in water to obtain a solution;
forming the solution into a film; and drying the film.

15. A film according to claim 14 which is an edible food packaging material.

16. A film according to claim 14 which is a casing for smoked food products.

17. A film according to claim 16 which is reinforced with a thin fibrous product.

18. A film according to claim 14 which is a shell for a soft capsule.

19. A film according to claim 14 which is a semipermeable membrane for separating a high-molecular weight substance from a low-molecular weight substance.

20. A film according to claim 19 which is reinforced with a thin fibrous product.

21. A film according to claim 14 which is a wound dressing.

22. A film according to claim 21 which is reinforced with a thin fibrous product.

23. An edible film prepared by a process comprising the steps of:
uniformly mixing glucomannan and other natural polysaccharides with a concentrated solution of at least one group of polyhydric alcohol;
dissolving the resulting glucomannan/polyhydric alcohol composition in water to obtain a solution;
mixing the solution with a food material to obtain a mixture;
forming the mixture into a film; and
drying the film.

24. An edible film according to claim 23 wherein the solution of at least one polyhydric alcohol has a concentration of 30-100 wt%.

25. An edible film prepared by a process comprising the steps of:
uniformly mixing glucomannan and other natural polysaccharides with a concentrated solution of at least one polyhydric alcohol in the presence of an alkali;
dissolving the resulting glucomannan/polyhydric alcohol composition in water to obtain a solution;
mixing the solution with a food material to obtain a mixture;
forming the mixture into a film; and
drying the film.

26. An edible film according to claim 25 wherein the solution of at least one polyhydric alcohol has a concentration of 30-100 wt%.

* * * * *